(12) United States Patent
Smith et al.

(10) Patent No.: US 6,641,534 B2
(45) Date of Patent: Nov. 4, 2003

(54) METHODS AND DEVICES FOR ULTRASOUND SCANNING BY MOVING SUB-APERTURES OF CYLINDRICAL ULTRASOUND TRANSDUCER ARRAYS IN TWO DIMENSIONS

(75) Inventors: Stephen W. Smith, Durham, NC (US); Edward D. Light, Durham, NC (US); Eric Christopher Pua, Guntersville, AL (US); Jesse T. Yen, Houston, TX (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/057,803

(22) Filed: Jan. 25, 2002

(65) Prior Publication Data

US 2003/0144591 A1 Jul. 31, 2003

(51) Int. Cl.[7] ................................................. A61B 8/00
(52) U.S. Cl. ........................................ 600/437; 600/454
(58) Field of Search ................................ 600/447, 437, 600/443, 444, 449, 454, 455, 456; 367/7, 11, 138

(56) References Cited

U.S. PATENT DOCUMENTS

| | | | |
|---|---|---|---|
| 5,027,820 A | | 7/1991 | Pesque |
| 5,902,241 A | * | 5/1999 | Seyed-Bolorforosh et al. .................... 600/443 |
| 6,102,860 A | | 8/2000 | Mooney |
| 6,120,449 A | * | 9/2000 | Snyder et al. .............. 600/447 |
| 6,419,633 B1 | * | 7/2002 | Robinson et al. ........... 600/443 |

* cited by examiner

Primary Examiner—Francis J. Jaworski
Assistant Examiner—Maulin Patel
(74) Attorney, Agent, or Firm—Myers Bigel Sibley & Sajovec, P.A.

(57) ABSTRACT

Methods of scanning using a two dimensional (2D) ultrasound transducer array are disclosed. The 2D ultrasound transducer arrays include at least one row of ultrasound transducer elements that is configured to extend in a curved dimension of the array and at least one column of ultrasound transducer elements that is configured to extend in a linear dimension of the array. A 2D ultrasound transducer array can be used to scan by defining a sub-aperture of the 2D ultrasound transducer array that includes a plurality of ultrasound transducer elements in the curved dimension of the array and in the linear dimension of the array and exciting the ultrasound transducer elements included in the sub-aperture to generate a transmit/receive ultrasound beam. Related 2D ultrasound transducer arrays and elements are also disclosed.

22 Claims, 10 Drawing Sheets

METHODS AND DEVICES FOR ULTRASOUND SCANNING BY MOVING SUB-APERTURES OF CYLINDRICAL ULTRASOUND TRANSDUCER ARRAYS IN TWO DIMENSIONS

STATEMENT OF GOVERNMENT SUPPORT

This invention was made with Government support under grant number CA56475 from the National Institutes of Health. The Government has certain rights to this invention.

FIELD OF THE INVENTION

The invention relates to the field of imaging in general, and more particularly, to ultrasound imaging.

BACKGROUND OF THE INVENTION

It is known to provide ultrasound images by scanning with different types of ultrasound transducer arrangements. For example, B mode images can be produced by linear phased arrays which scan a sector of a region as shown in FIG. 1. Linear sequential arrays can also be used to scan a rectangular region, as shown in FIG. 2, by transmitting a ultrasound beam orthogonal to a face of the array to produce a scan where the width region scanned is approximately rectangular. For example, the length of the region scanned by a linear rectangular array can be equal to the length of the array. Curved arrays can also be used to provide scans resembling a trapezoidal field of view.

Also, sectored phased arrays, transesophagael sectored phased arrays, catheter mounted intracardiac sectored phased arrays, catheter mounted Intravascular Ultrasound (IVUS) circular arrays, endoscopic arrays, and laporascopic arrays have all be used to provide B-mode ultrasonic imaging.

It is also known to provide three dimensional, or volumetric, ultrasound images using two dimensional ultrasound transducer arrays. For example, U.S. Pat. No. 4,694,434 to von Ramm and Smith discloses a steered phased array acoustic imaging scanner that provides a pyramidal volumetric scan of a region using a two dimensional ultrasound transducer array. U.S. Pat. No. 5,546,807 to Oxaal et al. discloses the display of images obtained from a volumetric scanner in which slices of the region scanned can be displayed in real time. U.S. Pat. No. 5,704,361 to Seward et al. discusses a 2D ultrasound transducer array on a catheter for intracardiac and general intraluminal volumetric scanning. U.S. Pat. No. 4,596,145 to Smith and von Ramm discloses an acoustic imaging system that can provide rectilinear volumetric images using a two dimensional ultrasound transducer array.

High-speed ultrasound volumetric imaging system part I: transducer design and beam steering, *IEEE Trans. Ultras. Ferro. And Freq. Control*, vol. 38, pp. 100–108, 1991, by Smith, S. W., Pavy, H. E., and von Ramm, O. T., discusses Mills cross 2D arrays used to provide steered pyramidal volumetric scanning. U.S. Pat. No. 5,901,708 to Song et al. also discussed Mills cross arrays.

SUMMARY OF THE INVENTION

Method embodiments according to the invention can provide ultrasound scans using two dimensional (2D) ultrasound transducer arrays. Pursuant to these method embodiments of the invention, the 2D ultrasound transducer arrays include at least one row of ultrasound transducer elements that is configured to extend in a curved dimension of the array and at least one column of ultrasound transducer elements that is configured to extend in a linear dimension of the array. A 2D ultrasound transducer array can be used to scan by defining a sub-aperture of the 2D ultrasound transducer array that includes a plurality of ultrasound transducer elements in the curved dimension of the array and in the linear dimension of the array and exciting the ultrasound transducer elements included in the sub-aperture to generate a transmit/receive ultrasound beam.

In some embodiments according to the invention, a first apodization function is applied to at least one row of ultrasound transducer elements that extend in the curved dimension included in the sub-aperture and a second apodization function is applied to at least one column of ultrasound transducer elements that extend in the linear dimension included in the sub-aperture.

In some embodiments according to the invention, the first apodization function includes a plurality of first excitation pulses having respective amplitudes that define a first raised cosine function a respective one of which is configured to be applied to a respective one of the plurality of the ultrasound transducer elements in the at least one row of ultrasound transducer elements. The second apodization function includes a plurality of second excitation pulses having respective amplitudes that define a second raised cosine function respective ones of which is configured to be applied to respective ones of the plurality of the ultrasound transducer elements in the at least one column of ultrasound transducer elements.

In some embodiments according to the invention, the sub-aperture is defined by selecting a plurality of first ultrasound transducer elements in the at least one row of ultrasound transducer elements and selecting a plurality of second ultrasound transducer elements in the in the at least one column of ultrasound transducer elements.

In some embodiments according to the invention, the sub-aperture is a first sub-aperture, the plurality of ultrasound transducer elements is a plurality of first ultrasound transducer elements, and the transmit/receive ultrasound beam is a first transmit/receive ultrasound beam. Other embodiments further include defining a second sub-aperture of the ultrasound transducer array that includes a plurality of second ultrasound transducer elements in the curved dimension of the array and in the linear dimension of the array and exciting the plurality of second ultrasound transducer elements included in the second sub-aperture to generate a second transmit/receive ultrasound beam.

In some embodiments according to the invention, a region is scanned in three dimensions based on the first and second transmit/receive ultrasound beams. In some embodiments according to the invention, an ultrasound transducer array carrier includes a curved surface that extends in a first dimension of the 2D ultrasound transducer array carrier and a linear surface that extends in a second dimension of the 2D ultrasound transducer array carrier. A 2D ultrasound transducer array is on the carrier and extends in the first and second dimensions of the ultrasound transducer array carrier, wherein the 2D ultrasound transducer array is configured to provide a moveable sub-aperture of the 2D ultrasound transducer array that is moveable in the first and second dimensions.

In some embodiments according to the invention, the 2D ultrasound transducer array includes a plurality of spaced-apart columns of ultrasound transducer elements and a plurality of spaced-apart rows of ultrasound transducer elements to define a plurality of Mills cross arrays. In some embodiments according to the invention, the 2D ultrasound transducer array includes one column of ultrasound transducer elements and one row of ultrasound transducer elements to define a Mill cross array.

In other embodiments according to the invention, an ultrasound transducer element has a curved face that is configured to generate a transmit/receive ultrasound beam from the curved face of the ultrasound transducer element. The ultrasound transducer carrier can have a curved surface, wherein the ultrasound transducer element is on the curved surface of the ultrasound transducer carrier wherein the curved face of the ultrasound transducer element faces away from the curved surface of the ultrasound transducer carrier.

In some embodiments according to the invention, a curvature of the curved face of the ultrasound transducer element and a curvature of the curved surface of the ultrasound transducer carrier can match one another.

DETAILED DESCRIPTION OF EMBODIMENTS OF THE INVENTION

Figure 1:
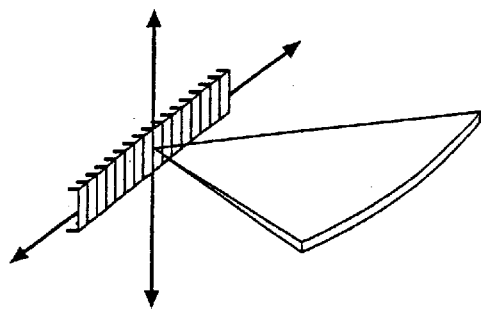
FIGS. 1 and 2 are a schematic diagrams of conventional linear arrays.
Figure 2:
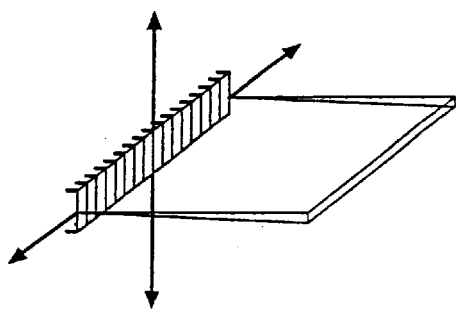

The invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In the drawings, the relative and/or absolute sizes of elements may be exaggerated for clarity. It will be understood that when an element such as an ultrasound transducer element is referred to as being "on" another element, it can be directly on the other element or intervening elements may also be present. In contrast, when an element is referred to as being "directly on" another element, there are no intervening elements present. The terms used herein are to be given their ordinary meaning unless explicitly defined otherwise herein.

As will be appreciated by one of skill in the art, the invention may be embodied as methods or devices. Accordingly, the invention may take the form of a hardware embodiment, a software embodiment or an embodiment combining software and hardware aspects.

The invention is also described using a flowchart illustration. It will be understood that each block of the flowchart illustration, and combinations of blocks, can be implemented by computer program instructions. These program instructions may be provided to a processor(s) within an ultrasound scanner, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 3:
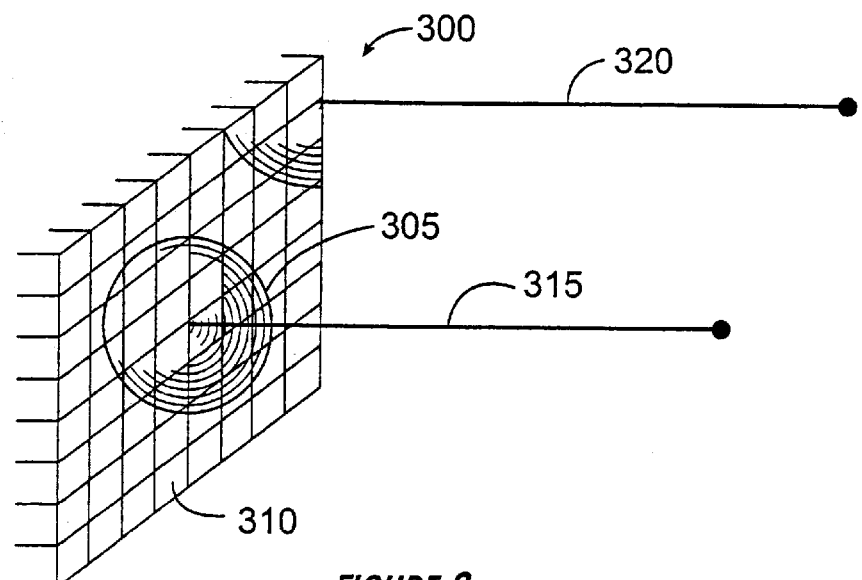
FIG. 3 is a schematic diagram of a two dimensional ultrasound transducer array having an apodization function applied thereto that excites selected ultrasound transducer elements of the array to create a moveable sub-aperture within the array.

FIG. 3 is a schematic diagram of a two dimensional ultrasound transducer array 300 having an apodization function 305 applied to selected ultrasound transducer elements 310 of the array 300 to define a sub-aperture of the array 300. In particular, the apodization function 305 applies an amplitude, in a transmit mode and/or in a receive mode, to each of the ultrasound transducer elements 310 that are defined to be included in the sub-aperture. The applied amplitudes of the apodization function 305 approximate a raised cosine function which ranges in value between about 0.0 (applied to the ultrasound transducer elements 310 located near the outer edge (or edges) of the sub-aperture, to about 1.0 (applied to the ultrasound transducer elements 310 located near the center of the sub-aperture). The closer an ultrasound transducer element 310 is located to the center of the sub-aperture, the more the amplitude of the applied excitation pulse is increased towards the maximum of 1.0 at the center of the sub-aperture.

Figure 4:
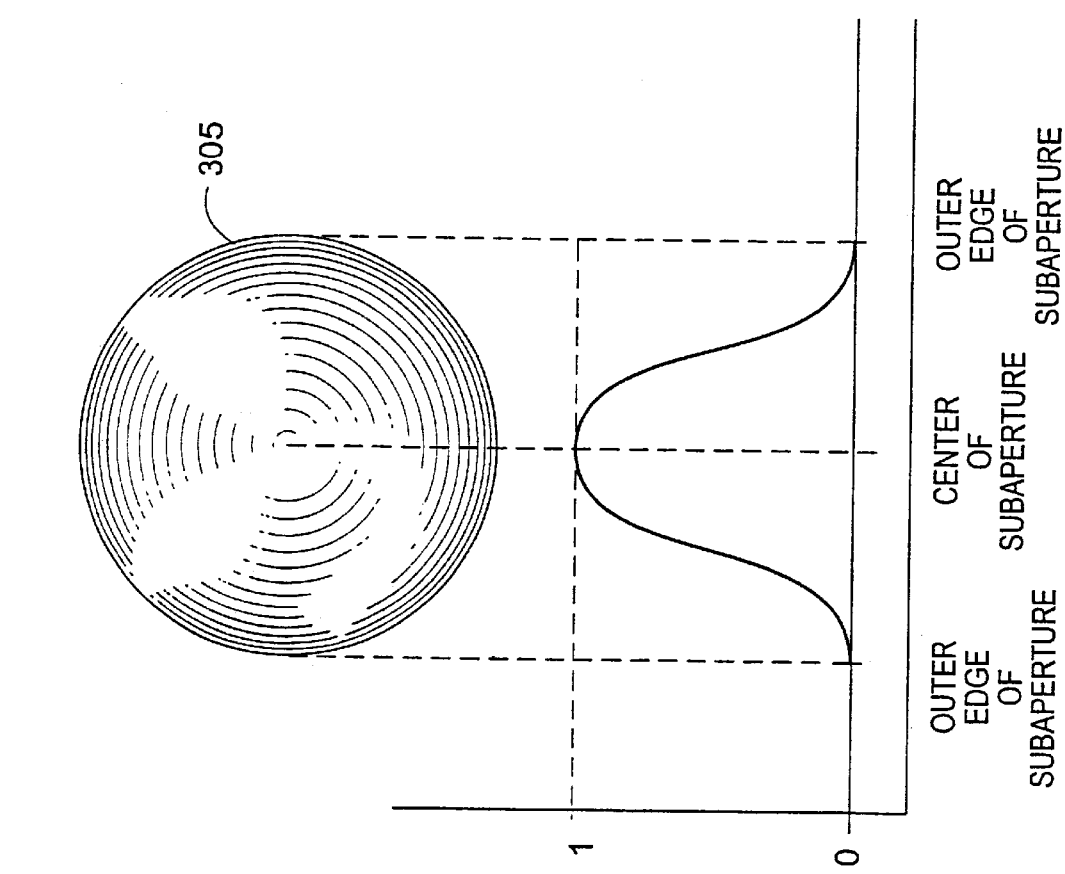
FIG. 4 is a scale that illustrates a range of amplitudes applied to the selected ultrasound transducer elements by the apodization function shown in FIG. 3.

The range of amplitudes applied to the ultrasound transducer elements by the apodization function are shown in FIG. 4 as a function of the element's location within the sub-aperture. A lighter shade indicates a higher amplitude of excitation and a darker shade indicates a lower amplitude of excitation. In other embodiments according to the invention, the apodization function applies excitations of equal amplitude to all of the ultrasound transducer elements in the sub-aperture regardless of where the ultrasound transducer elements are located in the sub-aperture. It will be understood that the amplitudes of the apodization function are applied substantially simultaneously to the ultrasound transducer elements 310 defined to be within a sub-aperture. For example, if nine of the ultrasound transducer elements 310 are defined to be within the sub-aperture used to generate a transmit/receive ultrasound beam, the amplitudes of the applied apodization functions are applied to the nine ultrasound transducer elements 310 substantially simultaneously. It will be further understood that the apodization functions used to generate the transmit/receive ultrasound beams can be applied in two dimensions of the ultrasound transducer array substantially simultaneously.

Referring again to FIG. 3, the apodization function 305 applied to the sub-aperture at the center of the array 300 is used to generate an "on-axis" transmit ultrasound beam 315 that originates from the center of the ultrasound transducer array 300 and is directed orthogonal to the face of the array 300. Furthermore, the sub-aperture can be moved throughout the array 300 by applying the apodization function 305 to a different set of ultrasound transducer elements 310. For example, as shown in FIG. 3, the sub-aperture can be moved within the array 300 by applying the apodization function 305 to the ultrasound transducer elements 310 in a corner of the array 300 to generate an "off-axis" transmit ultrasound beam 320.

Figure 5:
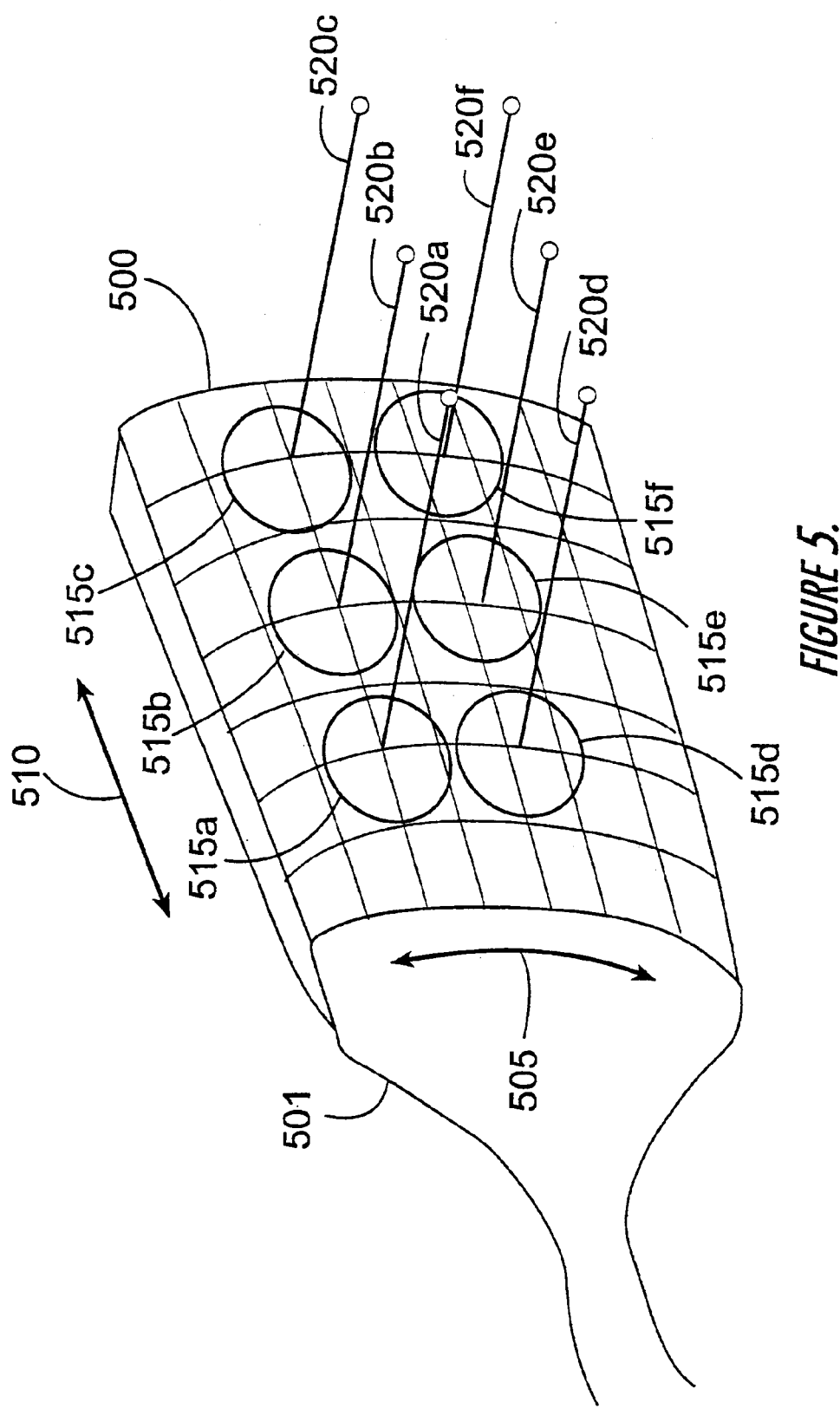
FIG. 5 is a schematic diagram of a cylindrical ultrasound transducer array having an apodization function applied in two dimensions thereto to create a moveable sub-aperture within the array according to embodiments of the invention.

FIG. 5 is a schematic diagram that illustrates an embodiment of a cylindrical two dimensional ultrasound transducer array 500 on an ultrasound transducer carrier 501 that is configured to provide a sub-aperture of the array 500 that moves in the two dimensions of the array 500 according to the invention. A first dimension 505 of the array 500 is curved and a second dimension 510 of the array 500 is linear to define the cylindrical shape of the array 500. It will be understood that the rows and columns can be orthogonal to one another or non-orthogonal to one another. It will also be understood that the cylindrical two dimensional ultrasound transducer array 500 can be a portion of an ultrasound transducer array that includes other portions that are not cylindrical.

The array 500 is configured to provide a sub-aperture of the array 500 that can be moved in the first and second dimensions 505, 510. Apodization functions can be applied sequentially to different sets of elements within the array 500 that are included in the different sub-apertures of the array 500. For example, as shown in FIG. 5, sub-apertures 515a–f can be provided by exciting the elements in the array 500 included in each the sub-apertures 515a–f. The sub-apertures 515a–f are used to generate corresponding transmit/receive ultrasound beams 520a–f respectively. In some embodiments according to the invention, the sub-apertures 515a–f can partially overlap one another.

Although FIG. 5 shows four adjacent transducer elements of the array 500 included in each of the sub-apertures 515a –f, it will be understood that the sub-apertures 515a –f can be defined to include more than four elements or fewer elements. Furthermore, in some embodiments according to the invention, the sub-apertures 515a –f can be defined to include non-adjacent elements of the array 500. In some embodiments according to the invention, the elements included in the sub-apertures 515a –f can define a circular ring of elements, a rectangular ring, a square ring of elements within the array 500. Other arrangements can be used.

Figure 6:
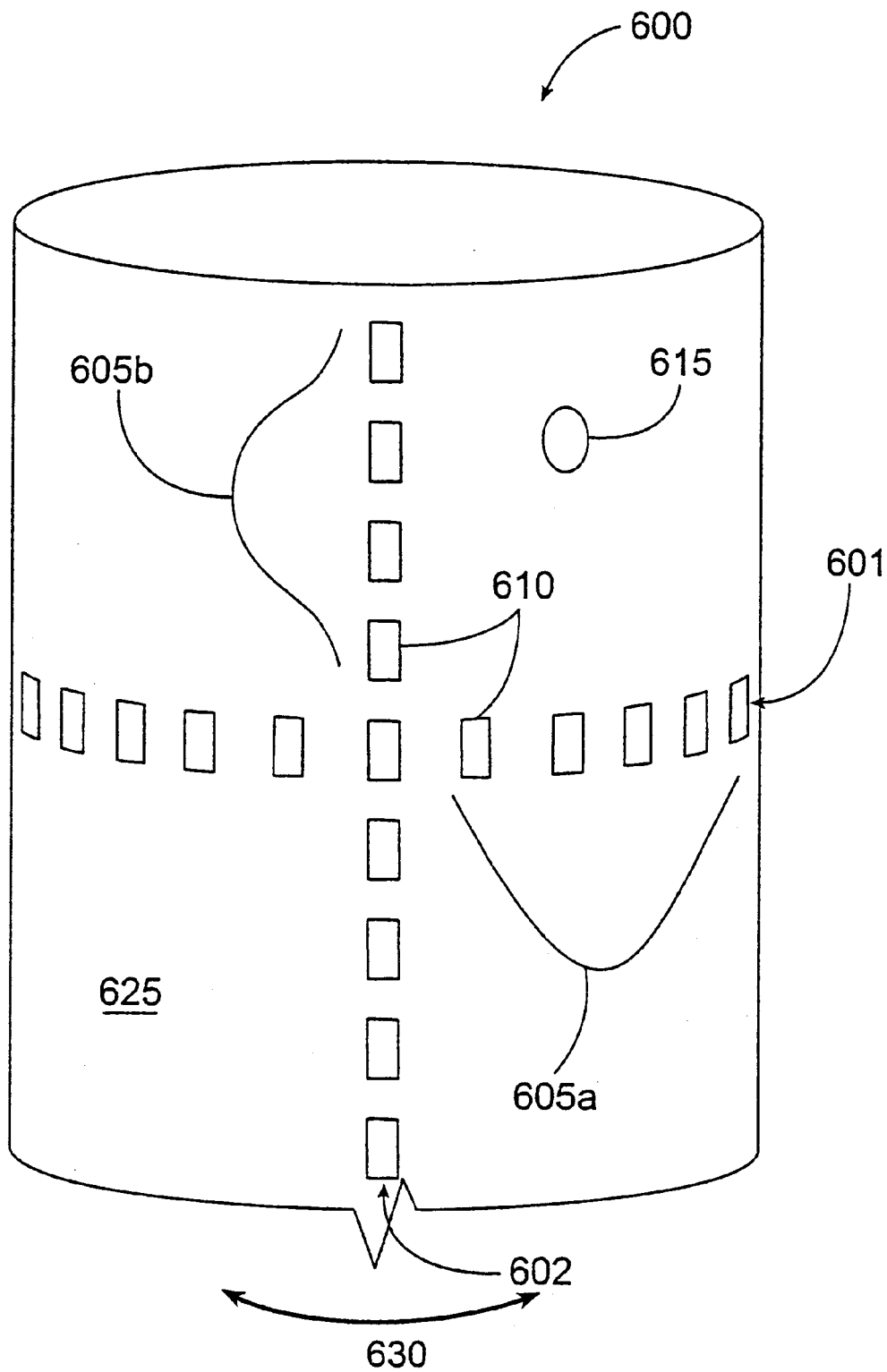
FIG. 6 is a schematic diagram of a Mills cross ultrasound transducer array having first and second apodization functions applied thereto according to embodiments of the invention.

FIG. 6 is a schematic drawing that illustrates embodiments of a two dimensional cylindrical ultrasound transducer Mills cross array 600 according to the invention. The array 600 extends in a row dimension 601 and in a column dimension 602 and is on a cylindrically shaped surface of an ultrasound transducer array carrier 625. The row dimension 601 and the column dimension 602 are offset from one another to define an angle therebetween. In some embodiments according to the invention, the offset angle can be an orthogonal angle or an acute angle.

The carrier 625 has a surface that is curved in a direction of curvature 630 in the row dimension 601 and that is linear in the column dimension 602 to define the cylindrical shape of the array 600. In some embodiments according to the invention, the carrier 625 is a probe, an endoscope, or other type of transducer probe on which the ultrasound transducer array 600 according to the invention is located. In some embodiments according to the invention, the carrier 625 can be a polyimide, an epoxy substrate, or the like.

As shown in FIG. 6, the array 600 includes one row of ultrasound transducers 610 that extend in the row dimension 601 which is curved and one column of ultrasound transducers 610 that extend in the column dimension 602 of the array 600, which is linear, to define a Mills cross array. The row of ultrasound transducers 610 extend on the surface to define an arc of curvature in a range between about 10 degrees and 360 degrees.

In some embodiments according to the invention, more rows and columns can be used to form the Mills cross array. According to embodiments of the invention, the row of ultrasound transducer elements 610 extend in the row dimension 601 in the direction of curvature 630.

In operation, first and second apodization functions 605a–b are applied to selected ones of the row and column ultrasound transducers 610, respectively, to create a sub-aperture within the array 600 to generate transmit/receive beams that are orthogonal to a face of the array 600. As shown in FIG. 6, when the maxima of the applied first apodization function 605a is centered on a right portion of the row ultrasound transducers 610 and the maxima of the applied second apodization function 605b is centered on an upper portion of the column of ultrasound transducers 610, a sub-aperture is created in an upper right quadrant of the array 600, which generates an off-axis transmit/receive beam 615 which is directed orthogonal to the array 600. It will be understood that in other embodiments, the sub-aperture can be created in other locations within the array 600 and can be moved within the array 600 to provide the ultrasound scanning.

Figure 7:
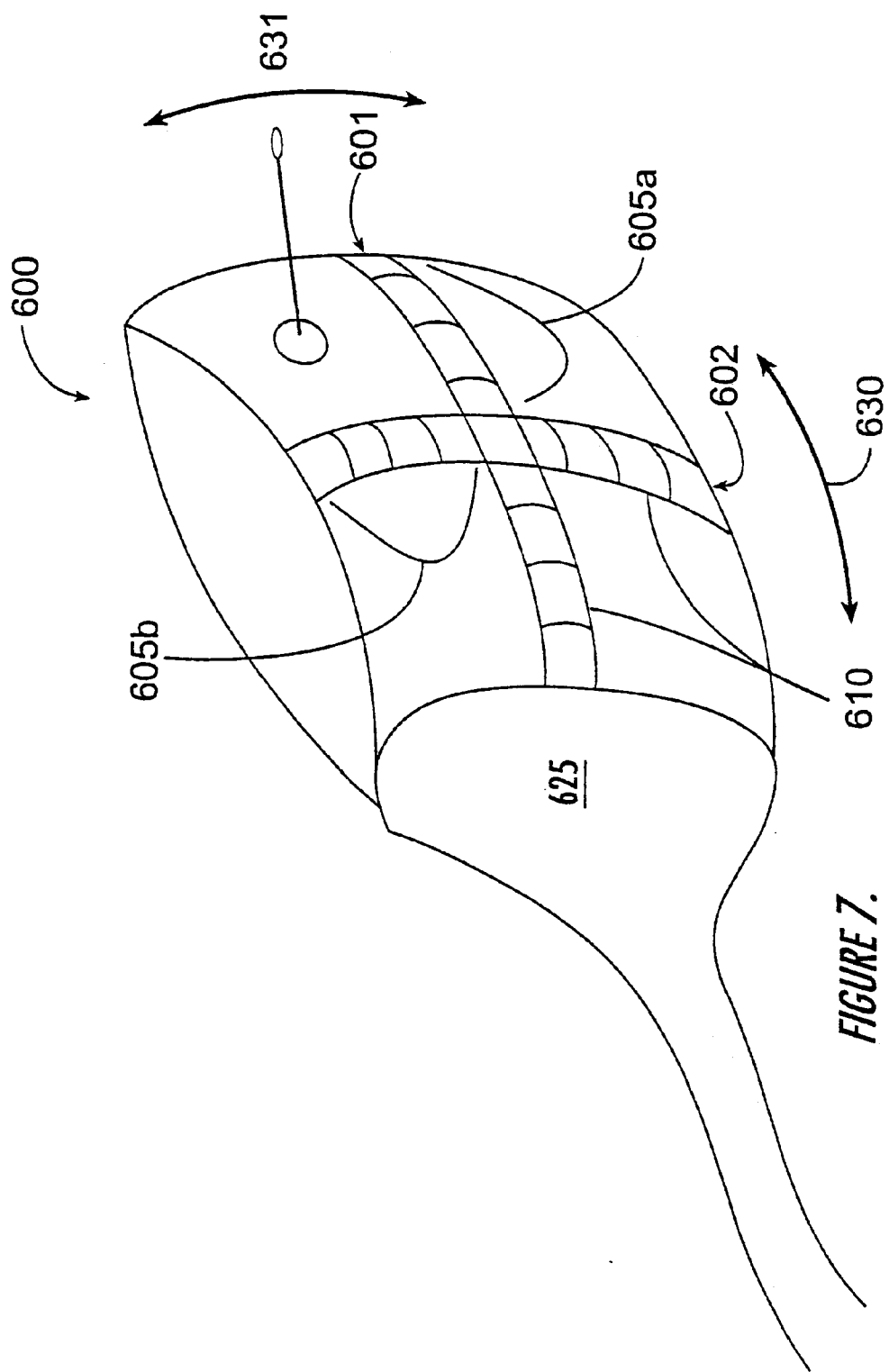
FIG. 7 is a schematic diagram of a Mills cross ultrasound transducer array on a surface that is curved in two-dimensions having first and second apodization functions applied thereto to provide an off-axis transmit/receive ultrasound beam according to embodiments of the invention.

As shown in FIG. 7, in some embodiments according to the invention, the surface of the carrier can be curved in the row and in the column dimensions so that the row of ultrasound transducer elements and the column of ultrasound transducer elements are curved in different directions of curvature to define the Mills cross array. As shown in FIG. 7, the surface of the carrier 625 is curved in a second direction of curvature 631 that is offset from the first direction of curvature 630. The row of ultrasound transducers follow the direction of curvature 630 and the column of ultrasound transducers follow the direction of curvature 631. Accordingly, both the columns and the rows or elements within the array are curved and define a Mill cross array.

Figure 8:
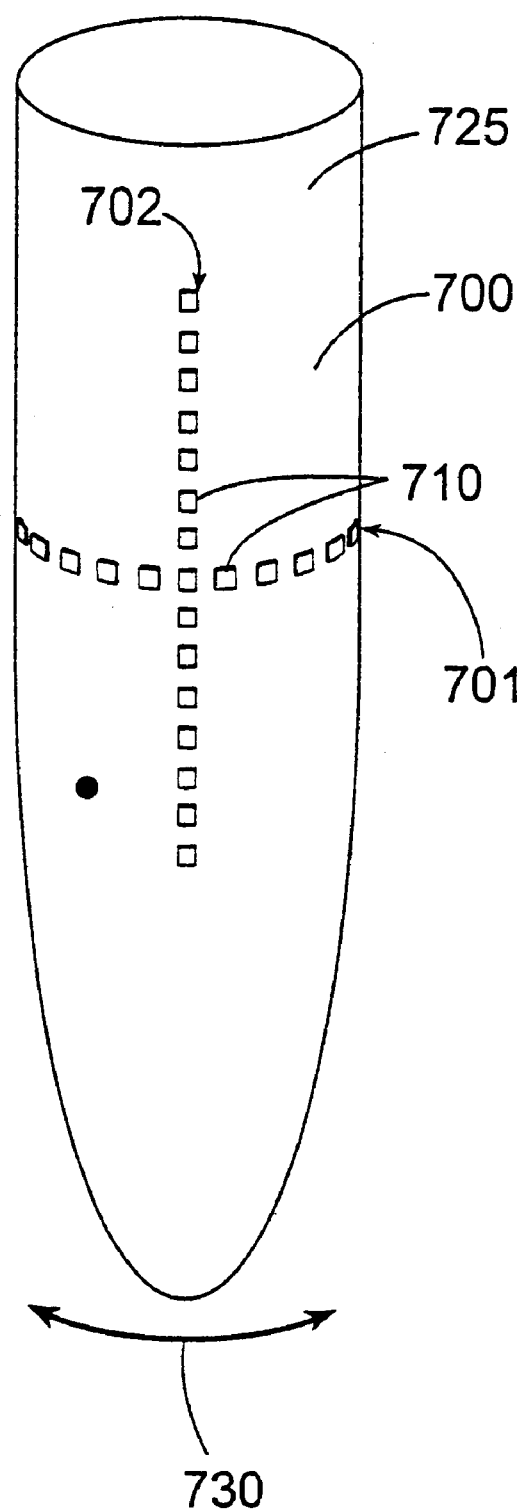
FIG. 8 is a schematic diagram of a Mills cross ultrasound transducer array on a cylindrical surface according to embodiments of the invention.

FIG. 8 is a schematic diagram that illustrates an embodiment of a cylindrical two dimensional ultrasound transducer array 700 to define a Mills cross array on a transducer probe 725 according to the invention. As shown in FIG. 8, the probe 725 has a surface which is curved in a direction of curvature 730. A row of ultrasound transducer elements 710 extends in a row dimension 701 of the array 700 which follows the direction of curvature 730 for about one half of the circumference of the probe 725. First and second apodization functions can be applied to the row and columns of the elements 710 to create a moveable sub-aperture of the array 700 which can provide a scan having a field of view of about 180 degrees. It will be understood that the transducer probe can be a catheter, and endoscope, or another type of probe.

Figure 9:
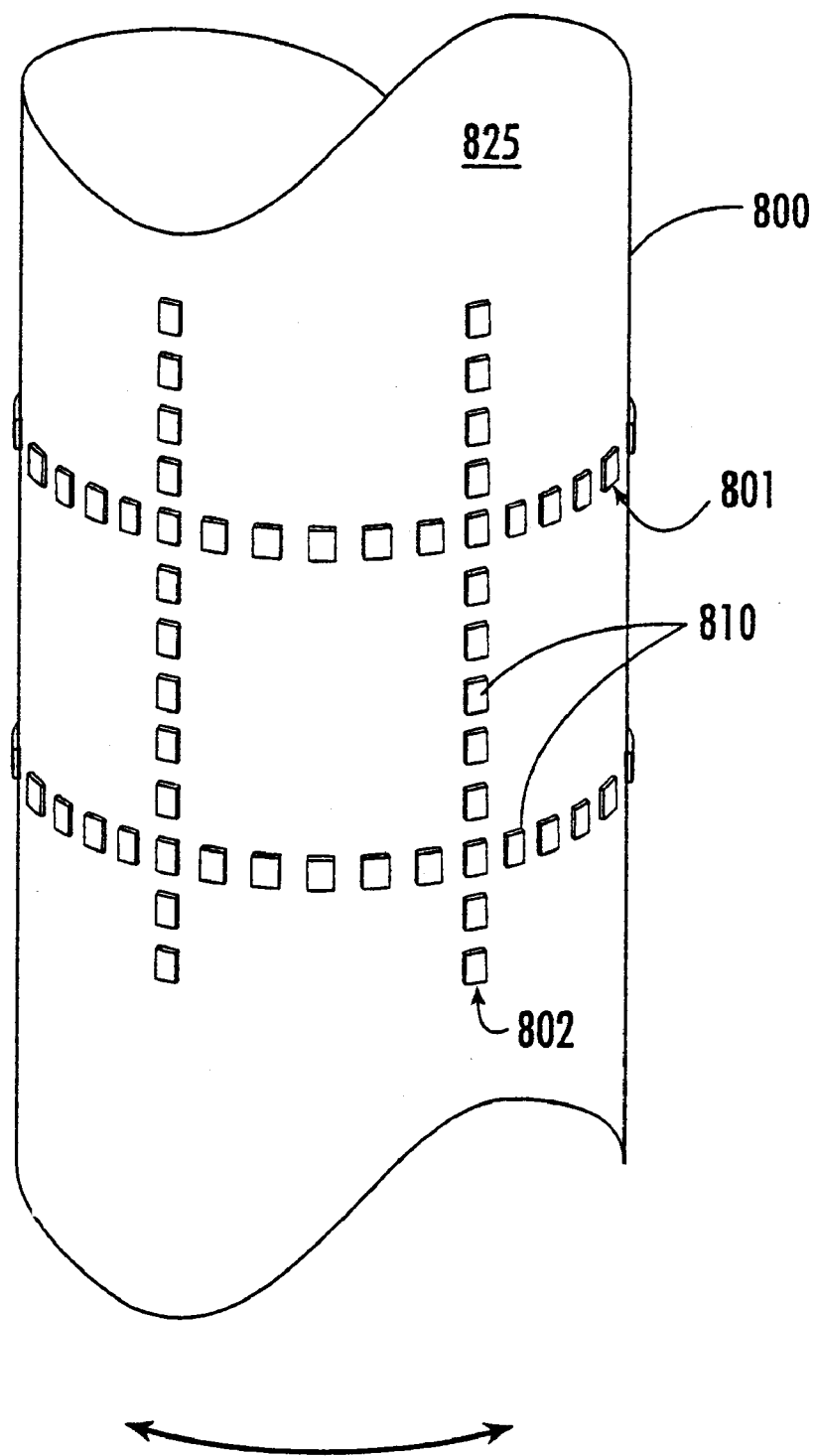
FIG. 9 is a schematic diagram of a Mills cross ultrasound transducer array including a plurality of spaced-apart rows and spaced-apart columns on a cylindrical surface according to embodiments of the invention.

FIG. 9 is a schematic diagram that illustrates embodiments of cylindrical two dimensional ultrasound transducer arrays 800 including a plurality of spaced-apart rows and spaced-apart columns of elements to define a Mill cross arrays according to the invention. As shown in FIG. 9, the array 800 includes a plurality of spaced-apart rows and columns of ultrasound transducer elements 810 which extend in row and column dimensions 801–802 of the array 800 respectively. An ultrasound transducer array carrier 825, on which the array 800 is located, has a cylindrically shaped surface that is curved in a direction of curvature 830. Accordingly, the plurality of spaced-apart rows of ultrasound transducer elements extend in the row dimension to define a curved row of elements on the surface of the carrier 825 in the direction of curvature 830. In some embodiments according to the invention, the plurality of spaced-apart rows and columns have a spacing of about 0.3 mm therebetween where an excitation pulse of about 5 Mhz is used to generate the ultrasound transmit/receive beams.

The spacing of the elements in the rows and columns disclosed herein can be provided according to the following equation:

$$\lambda = c/f$$

where $\lambda$ is the wavelength of the ultrasound transmit/receive beam generated in a medium, c is the speed of sound in the medium, and $f$ is the frequency of the excitation used to generate the ultrasound transmit/receive beam. The spacing of the rows and columns can be in a range between about $\lambda/10$ and $10\lambda$.

Figure 10:
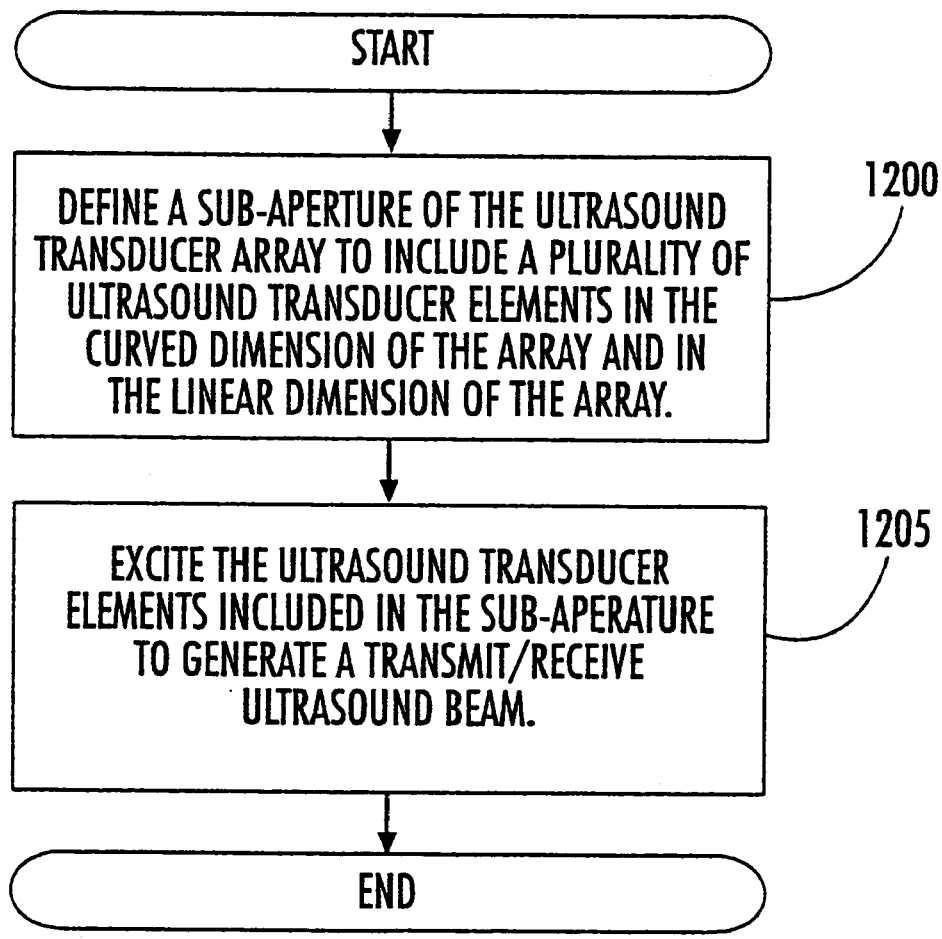
FIG. 10 is a flowchart that illustrates embodiments according to the invention.

FIG. 10 is a flowchart that illustrates embodiments according to the invention. According to FIG. 10, a sub-aperture of the ultrasound transducer array is defined to include a plurality of ultrasound transducer elements in the curved dimension of the array and in the linear dimension of the array (block 1200). The ultrasound transducer elements included in the sub-aperture are excited to generate a transmit/receive ultrasound beam (block 1205). In some embodiments according to the invention, the excitation is provided by applying a first apodization function to at least one row of ultrasound transducer elements and applying a second apodization function to at least one column of ultrasound transducer elements. The first and second apodization functions can include excitation pulses applied to the plurality of ultrasound transducer elements included in the sub-aperture.

Figure 11A:
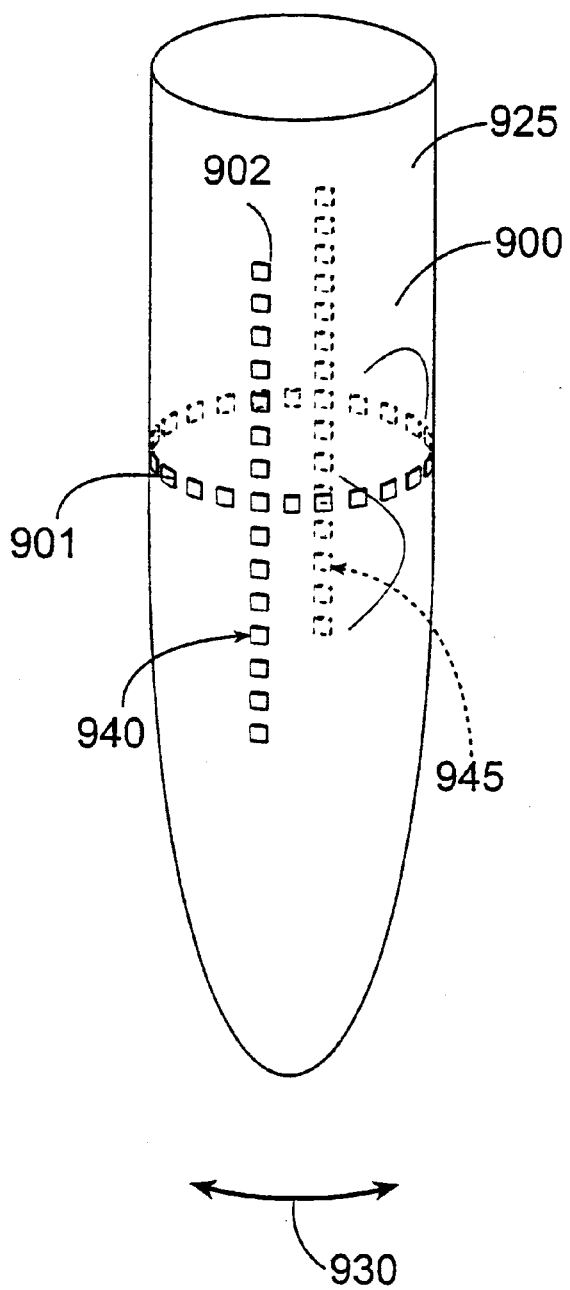
FIG. 11A is a schematic perspective diagram of a Mills cross ultrasound transducer array including two columns of transducer elements on a cylindrical surface according to embodiments of the invention.

FIG. 11A is a perspective schematic diagram that illustrates an embodiment of a cylindrical two dimensional ultrasound transducer array 900 on a probe 925 according to the invention. As shown in FIG. 11A, the array 900 includes at least one row of ultrasound transducer elements that extend in a row dimension of the array 900 which follows a curved surface of the probe 925 in a direction of curvature 930 around the circumference of the curved surface to provide a scan having a field of view of about 360 degrees.

Figure 11B:
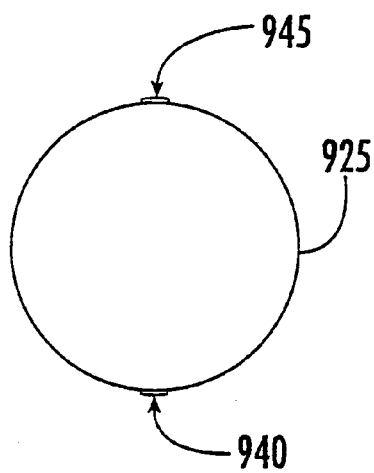
FIG. 11B is a schematic top view of the Mills cross ultrasound transducer array shown in FIG. 11A.

The array 900 includes first and second spaced-apart columns 940,945 of the ultrasound transducer elements 910 that are on opposing faces of the probe 925 and extend in a column dimension of the array 900 as illustrated in the top view of FIG. 11B. In some embodiments according to the invention, the first and second columns 940,945 are spaced-apart by about one-half of the circumference of the probe 925.

Figure 12:
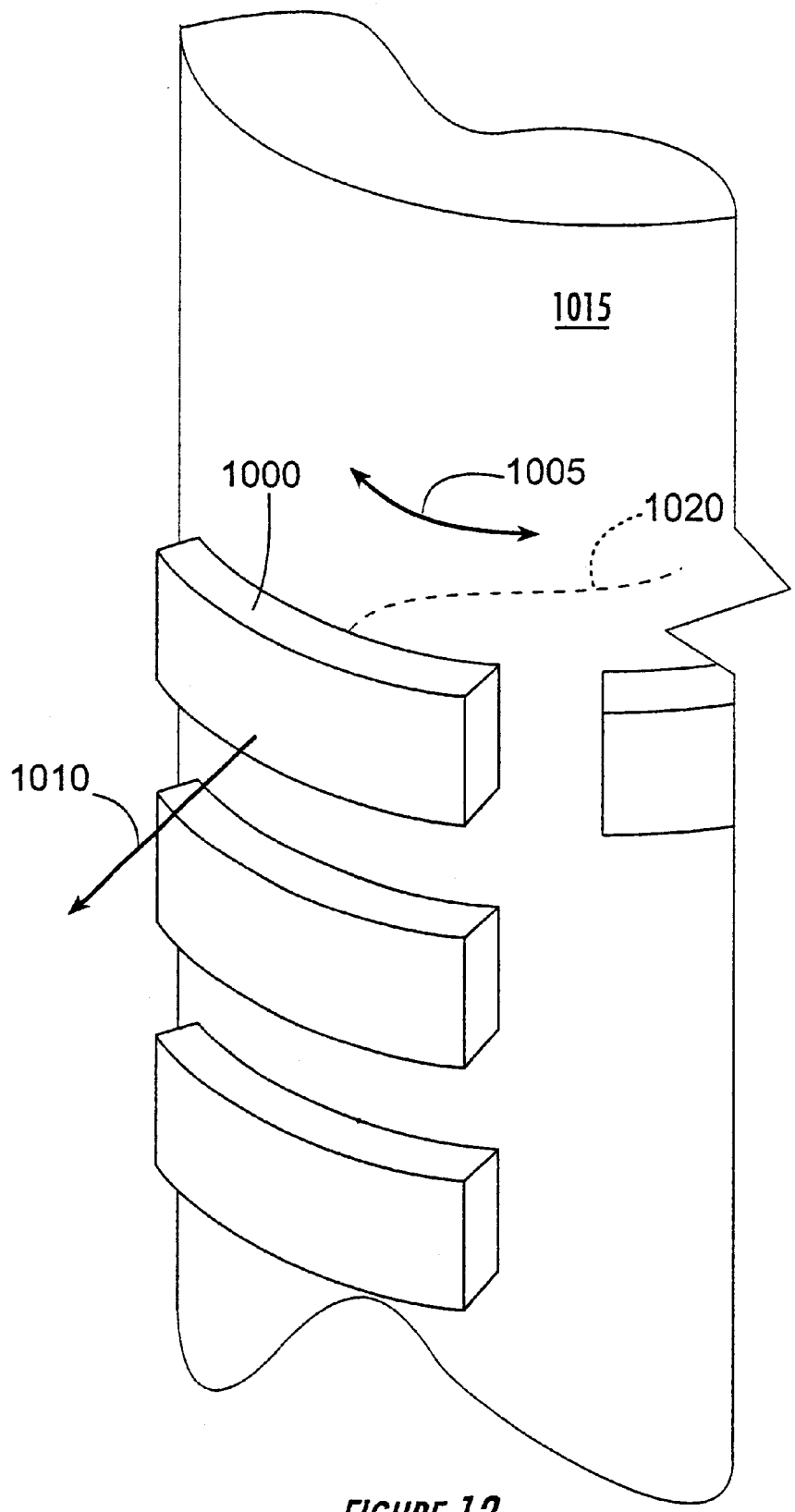
FIG. 12 is a schematic diagram of an ultrasound transducer element according to embodiments of the invention.

FIG. 12 is a schematic that illustrates an embodiment of an ultrasound transducer element 1000 in a two dimensional ultrasound transducer array according to the invention. The ultrasound transducer element 1000 can be used in any of the embodiments of ultrasound transducer arrays disclosed herein. The ultrasound transducer element 1000 is curved in a dimension 1005 to form a curved ultrasound transducer element 1000. The ultrasound transducer element 1000 is mounted on a surface of an ultrasound transducer carrier 1015 that is curved in the dimension 1005. The ultrasound transducer element 1000 can be configured to be electrically coupled to a single conductor 1020 via which an excitation can be applied to the ultrasound transducer element 1000 to generate an ultrasound transmit/receive beam 1010. The generated ultrasound transmit/receive beam 1010 is emitted from a face of the ultrasound transducer element 1000 that is curved in the dimension 1005. In some embodiments according to the invention the curvature of the ultrasound transducer element 1000 matches the curvature of the surface of an ultrasound transducer carrier 1015.

In the drawings and specification, there have been disclosed typical embodiments of the invention and, although specific terms are employed, they are used in a generic and descriptive sense only and not for purposes of limitation, the scope of the invention being set forth in the following claims.

What is claimed:

1. A method of scanning using a two dimensional (2D) ultrasound transducer array having at least one row of ultrasound transducer elements configured to extend in a curved dimension of the array and at least one column of ultrasound transducer elements configured to extend in a linear dimension of the array, the method comprising:

defining a sub-aperture of the ultrasound transducer array that includes a plurality of ultrasound transducer elements in the curved dimension of the array and a plurality of ultrasound transducer elements in the linear dimension of the array; and exciting the ultrasound transducer elements included in the sub-aperture to generate a transmit/receive ultrasound beam.

2. A method according to claim 1 wherein the exciting comprises:

applying a first apodization function to at least some of the plurality of ultrasound transducer elements that extend in the curved dimension included in the sub-aperture; and applying a second apodization function to at least some of the plurality of ultrasound transducer elements that extend in the linear dimension included in the sub-aperture.

3. A method according to claim 2:

wherein the first apodization function comprises a plurality of first excitation pulses having respective amplitudes that define a first raised cosine function configured to be applied to respective ones of the plurality of the ultrasound transducer elements in at least one row of ultrasound transducer elements; and wherein the second apodization function comprises a plurality of second excitation pulses having respective amplitudes that define a second raised cosine function configured to be applied to respective ones of the plurality of the ultrasound transducer elements in at least one column of ultrasound transducer elements.

4. A method according to claim 1 wherein the defining comprises:
selecting a plurality of first ultrasound transducer elements in the at least one row of ultrasound transducer elements; and
selecting a plurality of second ultrasound transducer elements in the in the at least one column of ultrasound transducer elements.

5. A method according to claim 1 wherein the sub-aperture comprises a first sub-aperture, the plurality of ultrasound transducer elements comprises a plurality of first ultrasound transducer elements, and the transmit/receive ultrasound beam comprises a first transmit/receive ultrasound beam, the method further comprising:
defining a second sub-aperture of the ultrasound transducer array that includes a plurality of second ultrasound transducer elements in the curved dimension of the array and in the linear dimension of the array; and
exciting the plurality of second ultrasound transducer elements included in the second sub-aperture to generate a second transmit/receive ultrasound beam.

6. A method according to claim 5 further comprising:
scanning a region in three dimensions based on the first and second transmit/receive ultrasound beams.

7. A two dimensional (2D) ultrasound transducer array comprising:
an ultrasound transducer array carrier having a curved surface that extends in a first dimension of the 2D ultrasound transducer array carrier and a linear surface that extends in a second dimension of the 2D ultrasound transducer array carrier; and
a 2D ultrasound transducer array on the carrier that extends in the first and second dimensions of the ultrasound transducer array carrier, wherein the 2D ultrasound transducer array is configured to provide a moveable sub-aperture of the 2D ultrasound transducer array that is moveable in the first and second dimensions.

8. A 2D ultrasound transducer array according to claim 7 wherein:
the 2D ultrasound transducer array includes a plurality of spaced-apart columns of ultrasound transducer elements and a plurality of spaced-apart rows of ultrasound transducer elements to define a plurality of Mills cross arrays.

9. A 2D ultrasound transducer array according to claim 7 wherein the 2D ultrasound transducer array includes one column of ultrasound transducer elements and one row of ultrasound transducer elements to define a Mill cross array.

10. A 2D ultrasound transducer array according to claim 9 wherein the one column of ultrasound transducer elements and the one row of ultrasound transducer elements are offset from one another to define an orthogonal angle therebetween.

11. A 2D ultrasound transducer array according to claim 9 wherein the one column of ultrasound transducer elements and the one row of ultrasound transducer elements define an acute angle with one another.

12. A 2D ultrasound transducer array according to claim 7 wherein the ultrasound transducer elements in the 2D ultrasound transducer array are only on a portion of the curved surface that defines an arc of curvature in a range between about 10 degrees and about 360 degrees.

13. A two dimensional (2D) ultrasound transducer array comprising:
an ultrasound transducer array carrier having a curved surface that extends in first and second dimensions of the 2D ultrasound transducer array;
a plurality of spaced-apart columns of ultrasound transducer elements included in the ultrasound transducer array configured to extend in the first dimension; and
a plurality of spaced-apart rows of ultrasound transducer elements included in the ultrasound transducer array configured to extend in the second dimension that is offset from the first dimension to define a Mills cross array.

14. A 2D ultrasound transducer array according to claim 13 wherein the ultrasound transducer array carrier further comprises a second curved surface that extends in the second dimension of the 2D ultrasound transducer array.

15. A two dimensional (2D) ultrasound transducer array comprising:
an ultrasound transducer array carrier having a curved surface that extends in at least a first dimension of the 2D ultrasound transducer array;
a single row of ultrasound transducer elements in the ultrasound transducer array configured to extend in the first dimension of the 2D ultrasound transducer array; and
a plurality of spaced-apart columns of ultrasound transducer elements in the ultrasound transducer array configured to extend in a second dimension of the 2D ultrasound transducer array that is offset from the first dimension.

16. A 2D ultrasound transducer array according to claim 15 wherein the ultrasound transducer elements in the 2D ultrasound transducer array are only on a portion of the curved surface that defines an arc of curvature in a range between about 10 degrees and about 360 degrees.

17. A 2D ultrasound transducer array according to claim 16 wherein the ultrasound transducer array carrier comprises one of a catheter or an endoscope.

18. An ultrasound transducer element comprising:
an ultrasound transducer element in a two dimensional ultrasound transducer array, the ultrasound transducer element having a curved face that is configured to generate a transmit/receive ultrasound beam from the curved face of the ultrasound transducer element.

19. An ultrasound transducer element according to claim 18 further comprising:
an ultrasound transducer carrier having a curved surface, wherein the ultrasound transducer element is on the curved surface of the ultrasound transducer carrier wherein the curved face of the ultrasound transducer element faces away from the curved surface of the ultrasound transducer carrier.

20. An ultrasound transducer element according to claim 19 wherein a curvature of the curved face of the ultrasound transducer element and a curvature of the curved surface of the ultrasound transducer carrier match one another.

21. An ultrasound transducer element according to claim 18 wherein ultrasound transducer element is configured to be excited by an apodization function to scan a region in three dimensions.

22. An ultrasound transducer element according to claim 18 further comprising:
a single conductor electrically connected to the ultrasound transducer element.

* * * * *

UNITED STATES PATENT AND TRADEMARK OFFICE
CERTIFICATE OF CORRECTION

PATENT NO. : 6,641,534 B2
DATED : November 4, 2003
INVENTOR(S) : Smith et al.

It is certified that error appears in the above-identified patent and that said Letters Patent is hereby corrected as shown below:

<u>Column 9,</u>
Line 7, should read -- elements in the at least one column of ultrasound --

Signed and Sealed this

Twenty-ninth Day of June, 2004

JON W. DUDAS
*Acting Director of the United States Patent and Trademark Office*